(12) United States Patent
Towe et al.

(10) Patent No.: US 11,058,900 B2
(45) Date of Patent: Jul. 13, 2021

(54) METHODS AND APPARATUS FOR TREATING A CERVIX WITH ULTRASOUND ENERGY

(71) Applicants: Dignity Health, San Francisco, CA (US); Arizona Board of Regents on Behalf of Arizona State University, Scottsdale, AZ (US)

(72) Inventors: Bruce C. Towe, Mesa, AZ (US); Robert E. Garfield, Goodyear, AZ (US); Shao-Qing Shi, Goodyear, AZ (US)

(73) Assignees: Dignity Health, San Francisco, CA (US); Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/820,838

(22) Filed: Nov. 22, 2017

(65) Prior Publication Data

US 2018/0093112 A1    Apr. 5, 2018

Related U.S. Application Data

(63) Continuation of application No. 14/651,009, filed as application No. PCT/US2013/074106 on Dec. 10, 2013, now abandoned.

(60) Provisional application No. 61/735,306, filed on Dec. 10, 2012.

(51) Int. Cl.
*A61N 7/00* (2006.01)
*A61B 8/08* (2006.01)
*A61B 90/00* (2016.01)

(52) U.S. Cl.
CPC .................. *A61N 7/00* (2013.01); *A61B 8/08* (2013.01); *A61B 2090/378* (2016.02); *A61N 2007/0043* (2013.01)

(58) Field of Classification Search
CPC .............. A61N 7/00; A61N 2007/0043; A61H 23/0245; A61B 2090/378; A61B 8/08
See application file for complete search history.

(56) References Cited

U.S. PATENT DOCUMENTS

| | | | |
|---|---|---|---|
| 5,851,188 A * | 12/1998 | Bullard | A61B 5/1076 600/448 |
| 5,991,649 A | 11/1999 | Garfield et al. | |
| 6,356,777 B1 * | 3/2002 | Garfield | A61B 5/04882 600/372 |

(Continued)

FOREIGN PATENT DOCUMENTS

| WO | 1999/40842 | 8/1999 |
|---|---|---|
| WO | 2010/06138 | 6/2010 |
| WO | 2012/058289 | 5/2012 |

OTHER PUBLICATIONS

FDA Guideline.*

(Continued)

*Primary Examiner* — Hien N Nguyen
(74) *Attorney, Agent, or Firm* — Quarles & Brady LLP

(57) ABSTRACT

Methods and apparatuses for speeding the softening of the cervix (cervical ripening) by way of application of ultrasound energy. A vaginal transducer may be used to emit pulse-modulated ultrasound energy directed to the cervix. Focused ultrasound energy may be applied transabdominally and directed at the cervix.

11 Claims, 6 Drawing Sheets

(56) References Cited

U.S. PATENT DOCUMENTS

| | | | |
|---|---|---|---|
| 8,897,871 | B2 | 11/2014 | Wagner et al. |
| 2006/0167500 | A1* | 7/2006 | Towe ................... A61N 1/32 607/3 |
| 2007/0232913 | A1* | 10/2007 | Lau ..................... A61N 7/022 600/439 |
| 2011/0178391 | A1* | 7/2011 | Fernandez ............ A61N 7/022 600/411 |
| 2011/0213200 | A1* | 9/2011 | Mishelevich ........... A61N 7/00 600/38 |
| 2013/0281890 | A1* | 10/2013 | Mishelevich .......... A61N 2/002 601/2 |
| 2013/0331905 | A1* | 12/2013 | Haessler ............. A61N 1/0514 607/41 |
| 2014/0211593 | A1* | 7/2014 | Tyler .................... A61B 5/165 367/137 |

OTHER PUBLICATIONS

Application of Low Frequency Focused Ultrasound Waves Ripen the Rat Cervix During Pregnancy (Year: 2012).*
Revell, WJ and Roberts, MG (1990). "Ultrasound effects on miniature end plate potential discharge frequency are contingent upon acoustic environment." Ultrasonics 28: 149-154.
Rinaldi, PC et al. (1991). "Modification by focused ultrasound pulsed of electrically evoked responses from an in vitro hippocampal preparation." Brain Research 558: 36-43.
Shi et al., "Changes in cervical resistance and collagen fluorescence during gestation in rats" J Perinat Med, 1999; 27(3):188-194.
Shi et al., "Studies of cervical ripening in pregnant rats: effects of various treatments" Mol Hum Reprod, 2000; 6(4):382-389.
Steer, P. (2005). "The epidemiology of preterm labour." BJOG 112 Suppl 1: 1-3.
Sun, Y., et al. (2008). "Development of a Multi-modal Tissue Diagnostic System Combining High Frequency Ultrasound and Photoacoustic Imaging with Lifetime Fluorescence Spectroscopy" Proc IEEE Ultrason Symp: 570-573.
Takagi, SF et al. (1959). "The actions of ultrasound on the myelinated nerve, the spinal cord and the brain." Jpn J Physiol 10: 183-193.
Takemura, M. et al (2005). "Cyclic mechanical stretch augments hyaluronan production in cultred human uterine cervical fibroblast cells." Molecular Human Reproduction 11: 659-665.
Ter Haar, D. (2007). "Therapeutic application of ultrasound." Progress in Biophysics and Molecular Biology(93): 111-129.
Tufail, M. et al. (2011). "Ultrasonic neuromodulation by brain stimulation with transcranial ultrasound." Nature Protocols 6(9): 2011.
Tufail, Y et al. (2010). "Transcranial pulsed ultrasound stimulates intact brain circuits." Neuron 66(5): 681-694.
Tyler et al., "Remote Excitation of Neuronal Circuits Using Low Intensity, Low Frequency Ultrasound", PLoS One, 3(10):e3511, 2008.
Uldbjerg, Net al. (1981). "Biochemical and morphological changes of human cervix after local application of prostaglandin E2 in pregnancy." Lancet 1(8214): 267-268.
Uldbjerg, Net al. (1983). "Ripening of the human uterine cervix related to changes in collagen, glycosaminoglycans, and collagenolytic activity." Am J Obstet Gynecol 147(6): 662-666.
Yoo et al., "Focused ultrasound modulates region-specific brain activity" Neuroimage, 2011; 56(3):1267-1275.
Yoo, SS et al. (2011). "Transcranial focused ultrasound to the thalamus alters anesthesia time in rats." Neuroreport 22(15): 783-787.
Young, RR and Henneman, E (1961). "Functional effects of ultrasound on mammalian nerves" Science 134: 1521-1522.
Dalecki, D. (2004). "Mechanical Bioeffects of Ultrasound." Annual Review of Biomedical Engineering 6: 229-248.
DeFranco, EA et al. (2007). "Vaginal progesterone is associated with a decrease in risk for early preterm birth and improved neonatal outcome in women with a short cervix: a secondary analysis from a randomized, double-blind, placebo-controlled trial." Ultrasound Obstet Gynecol 30(5):697-705.
Di Renzo "Progesterone and pregnancy" Current Opinion Obstet Gynecol, 2005; 17(6): 598-600.
Dinno, MA et al. (1989). The significance of membrane changes in the safe and effective use of therapeutic and diagnostic ultrasound. Physics in Medicine and Biology (34): 1543-1552.
Edrich, J. and T. Zhang (1993). Ultrasound focused neuromagnetic stimulation. Proc IEEE/EMDS 15th Ann Conf. San Diego(USA): 1253-1254.
Facchinetti, F et al. (2007). "Cervical length changes during preterm cervical ripening: effects of 17-alpha-hydroxyprogesterone caproate." Am J Obstet Gynecol 196(5): 453e 1-4.
Farny, CH et al. (2009). "Temporal and spatial detection of HIFU induced inertial and hot-vapor cavitation with a diagnostic ultrasound system." Ultrasound Med Biol 35(4): 603-615.
Fittkow et al., "Changes in light-induced fluorescence of cervical collagen in guinea pigs during gestation and after sodium nitroprusside treatment" J Perinat Med, 2001;29(6):535-543.
Fittkow, CT et al. (2005). "Light-induced fluorescence of the human cervix decreases after prostaglandin application for induction of labor at term." Eur J Obstet Gynecol Reprod Biol 123(1): 62-66.
Forester, GV et al. (1987). "Effect of therapeutic level ultrasound on visual evoked potentials in the hypoxic cat." Ultrasound Med Biol 13(5): 259-265.
Fry et al., "Production of reversible changes in the central nervous system by ultrasound" Science, 1958;127 :83-84.
Garfield et al., "Control and assessment of the uterus and cervix during pregnancy and labour" Hum Reprod Update, 1998; 4(5): 673-695.
Garfield, RE et al. (2002). "Uterine electromyography and light-induced fluorescence in the management of term and preterm labor." J Soc Gynecol Investig 9(5): 265-275.
Gavrilov et al., "Stimulation of human peripheral neural structures by focused ultrasound" Sov Phys Acoust, 1974;19(4): 332-334.
Gavrilov, LR et al. (1995). "Application of focused ultrasound for the stimulation of neural structures." Ultrasound Med Biol 22(2):179-192.
Glassman et al., "Changes in rat cervical collagen during gesta-tion and after antiprogesterone treatment as measured in vivo with light-induced autofluorescence" Am J Obstet Gynecol, 1995; 173:1550-1556.
Goldenberg, RL et al. (2008). "Epidemiology and causes of preterm birth." Lancet 371(9606): 75-84.
Harkness, ML and Harkness, RD (1959). "Changes in the physical properties of the uterine cervix of the rat during pregnancy." J Physiol 148: 524-547.
Harvey, EN (1929). "The effect of high frequency sound waves on heart muscle and other irritable tissues." American Journal of Physics 91: 284-290.
Heath et al., "Cervical length at 23 weeks of gestation: prediction of spontaneous preterm delivery" Ultrasound Obstet Gynecol, 1998 12(5): 312-317.
Iams et al., "The length of the cervix and the risk of spontaneous premature delivery" National Institute of Child Health and Human Development Maternal Fetal Medicine Unit Network., N Engl J Med, 1996;334(9): 567-572.
International Search Report and written opinion for PCT/US2013/074106 filed on Dec. 10, 2013.
Ji, H., et al. (2008). "Androgen-regulated cervical ripening: a structural, biomechanical, and molecular analysis." Am J. Obstet Gynecol 198(5): 543 el-e9.
Kleissl, HP et al. (1978). "Collagen changes in the human uterine cervix at parturition." Am J Obstet Gynecol 130(7): 748-753.
Kramer, JF (1985). "Effect of therapeutic ultrasound intensity on subcutaneous tissue temperature and ulnar nerve conduction velocity." Amer J Physical Med 64(1): 1-9.
Kuon et al., "Pharmacologic actions of progestins to inhibit cervical ripening and prevent delivery depend on their properties, the route of administration, and the vehicle" Am J Obstet Gynecol, 2010; 202(5):455.el-e9.

(56) References Cited

OTHER PUBLICATIONS

Leighton, TG (2007). "What is ultrasound." Progress in Biophysics and Molecular Biology: 3-83.
Lele, PP (1963). "Effects of focused ultrasonic radiation on peripheral nerve with observations on local heating." Exp Neurol 8: 47-83.
Leppert, PC. "Cervical softening, effacement and dilatation: A complex biochemical cascade" J Maternal-Fetal Med, 1992; 1: 213-223.
Lockwood, CJ and Kuczynski, E(2001). "Risk stratification and pathological mechanisms in preterm delivery." Paediatr Perinat Epidemiol 15 Suppl 2: 78-89.
Ludwig, GG. "The velocity of sound through tissues and the acoustic impedance of tissues" J Acoust Soc Am, 1950; 22: 862-866.
Mason, T. (2011). "Therapeutic ultrasound an overview" Ultrasonics Sonochemistry 18(4):847-852.
Maul et al., "Local application of platelet-activating factor induces cervical ripening accompanied by infiltration of polymorphonuclear leukocytes in rats" Am J Obstet Gynecol, 2002; 187(4): 829-833.
Mihran, RT et al. (1990). "Temporally-specific modofocation of myelinated axon excitability in vitro following a single ultrasound pulse." Ultrasound Med Biol 16(3): 297-309.
Mihran, RT et al. (1990). "Transient modification of membrane potential and conductance by single ultrasound burts modulates neuronal excitability." Annu Int Conf IEEE Eng Med Biol 12(1): 447-448.
Norwitz et al., "Reviews in obstetrics & gynecology goes global: building ties with china" Rev Obstet Gynecol, 2011; 4(1):1-2.
Norwitz, ER and Caughey, AB (2011). "Progesterone supplementation and the prevention of preterm birth." Rev Obstet Gynecol 4(2): 60-72.

O'Brien, WDJ (2007). "Ultrasound-biophysics mechanisms." Progress in Biophysics and Molecular Biology(93): 212-255.
Owen, J., et al. (2003). "Vaginal sonography and cervical imcompetence." Am J Obstet Gynecol 188(2): 586-596.
Paliwal, S. et al. (2008). "Therapeutic opportunities in biological responses of ultrasound" Ultrasonics 48(4): 271-278.
Phillips, WB. (2008). High frequency ultrasound modifications to the electrical activation of neural tissue, Arizona State University. Doctor of philosophy thesis.
Rechberger, T et al. (1988). "Connective tissue changes in the cervix during normal pregnancy and pregnancy complicated by cervical incompetence." Obstet Gynecol 71(4): 563-567.
Bachtold, MR, et al. (1998). "Focused ultrasound modifications of neural circuit activity in a mammalian brain." Ultrasound Med Biol 24(4): 557-565.
Bigelow et al. In-vivo Ultrasonic Attenuation Slope Estimates for Detecting Cervical Ripening in Rats: Preliminary Results. (2008) J Acoust Soc Am. March, vol. 123(3); pp. 1794-1800.
Bystritsky et al., (2011). "A Review of Low Intensity Focused Ultrasound Pulsation," Brain Stimulation, vol. 4, No. 3, pp. 125-136.
CDRH (2008). "Information for manufacturers seeking marketing clearance of diagnostic ultrasound systems and transducers" Guidance for Industry and FDA Staff.
Clark, K. et al. (2006). "Mifepristone-induced cervical ripening: structural, biomechanical, and molecular events." Am J Obstet Gynecol, 194(5): 1391-1398.
Colucci et al., "Focused ultrasound effects on nerve action potential in vitro" Ultrasound Med Biol, 2009; 35: 1737-1747.
Crum, L. et al. (2010). "Therapeutic ultrasound: Recent trends and future perspectives" Physics Procedia 3(1):25-34.
Dalecki et al., "Effects of pulsed ultrasound on the frog heart: thresholds for changes in cardiac rhythm and aortic pressure" Ultrasound Med Biol, 1993; 19(5): 385-390.

\* cited by examiner

METHODS AND APPARATUS FOR TREATING A CERVIX WITH ULTRASOUND ENERGY

CROSS-REFERENCE TO RELATED APPLICATION

This application is a continuation of U.S. patent application Ser. No. 14/651,009 filed Jun. 10, 2015, which is a national phase application under 35 U.S.C. § 371 of International Application No. PCT/US2013/074106 filed Dec. 10, 2013, which claims the benefit of U.S. Provisional Patent Application No. 61/735,306 entitled "Methods and Apparatuses for Treating a Cervix With Ultrasound Energy," filed on Dec. 10, 2012, which are specifically incorporated herein by reference without disclaimer in their entirety.

BACKGROUND

1. Field of the Invention

This disclosure relates generally to methods and apparatus for the practice of medical obstetrics. More particularly, this disclosure relates to methods and apparatus for treating a cervix using ultrasound energy.

2. Description of Related Art

Ultrasound energy is widely used in medical applications such as diagnostic imaging, therapeutic heating and noninvasive surgery. Ultrasound diagnostic imaging employs sound power levels and pulse protocols considered safe for use in obstetrics. Its long history of use in the clinic supports this conclusion. At much higher ultrasound power levels, the vibration of tissue can produce warmth and heating which is useful in the treatment of soft tissue injuries and certain arthritic conditions. There are also ultrasound based devices that use relatively high intensity focused energy for thermal treatment of cancers.

Ultrasound energy levels used in medical imaging are characterized by their mechanical effects where avoidance of cavitation is important and also by their thermal effects on tissues. The mechanical effects of ultrasound absorption are also known as non-thermal effects and are represented by the mechanical index (MI), which is a relative measure. The mechanical index (MI) is defined as the maximal value of the peak negative pressure of the ultrasound wave measured in milliPascals divided by the square root of the acoustic center frequency of the ultrasound wave. Regulatory standards in the United States require the MI to be below 1.9 to avoid cavitation. The ultrasound power delivery known as $I_{SPTA.3}$ is a derated spatial peak temporal average. There are different permissible values of this depending on the target organ exposed to ultrasound. The most commonly cited value is 720 m W/cm$^2$ $I_{SPTA.3}$ and 190 W/cm$^2$ $I_{SPPA.3}$ for exposure to the body (US FDA, Guidance for Industry and FDA Staff: Information for Manufacturers Seeking Marketing Clearance of Diagnostic Ultrasound Systems and Transducers, Document issued on: Sep. 9, 2008). This value is lower for direct ultrasound exposure of the fetus. Another measure of thermal effects is the thermal index (TI), which is a calculated estimate of temperature increase with tissue absorption of ultrasound and is defined as the ratio of the emitted acoustic power to the power required to raise the temperature of tissue by 1° C. Regulatory standards in the United States require the TI to be below 1.0.

Ultrasound imaging machines emit microsecond-order pulses into tissues at a repetition rate that typically does not exceed 4 kHz and thus the duty cycle of the ultrasound energy is relatively low, on the order of less than one percent. In addition, ultrasound imaging examinations are conducted over short intervals of time, typical minutes, and the overall ultrasound integrated dose to a patient is relatively low. Ultrasound imaging is briefly described below.

Ultrasound imaging (sonography) uses high-frequency sound waves to view soft tissues such as muscles and internal organs. Because ultrasound images are captured in real-time, they can show movement of the body's internal organs as well as blood flowing through blood vessels.

In an ultrasound exam, a hand-held transducer is placed against the skin. The transducer sends out high frequency sound waves that reflect off of body structures. The returning sound waves, or echoes, are displayed as an image on a monitor. The image is based on the frequency and strength (amplitude) of the sound signal and the time it takes to return from the patient to the transducer. Unlike with an x-ray, there is no ionizing radiation exposure with this procedure.

Ultrasound imaging is used in many types of examinations and procedures. Some examples include:
a) Doppler ultrasound (to visualize blood flow through a blood vessel);
b) bone sonography (to diagnose osteoporosis);
c) echocardiogram. (to view the heart);
d) fetal ultrasound (to view the fetus in pregnancy);
e) ultrasound imaging of the cervix during pregnancy (short cervix is risk factor for preterm birth)
f) ultrasound-guided biopsies; and
g) Doppler fetal heart rate monitors (to listen to the fetal heart beat).

Ultrasound imaging has been used for over 20 years and has an excellent safety record. It is non-ionizing radiation, so it does not have the same risks as x-rays or other types of ionizing radiation. Even though there are no known risks of ultrasound imaging, it can produce effects on the body. When ultrasound enters the body, it heats the tissues slightly. In some cases, it can also produce small pockets of gas in body fluids or tissues (cavitation). Because of the particular concern for fetal exposures, national and international organizations have advocated prudent use of ultrasound imaging. Furthermore, the use of diagnostic ultrasound for non-medical purposes such as fetal keepsake videos has been discouraged. Ultrasound imaging is used routinely in obstetrics to visualize the cervix in pregnant patients. Transvaginal ultrasound imaging has now established that the shorter the sonographic cervical length in the mid-trimester, the higher the risk of preterm delivery. Indeed, it is possible to assign an individualized risk for preterm delivery using sonographic cervical length and other maternal risk factors, such as maternal age, ethnic group, body mass index and previous cervical surgery. Among these factors, sonographic cervical length is thought to be one of the most powerful predictors for preterm birth in the index pregnancy, and is more informative than a history of previous preterm birth.

Pulses of longer duration ultrasound, on the order of milliseconds and at repetition rates much lower while still emitting power levels within MI and $I_{SPTA.3}$ safety limits can produce bioelectrical stimulatory and in some cases inhibitory effects on the central nervous system. See, e.g., Tyler, W. J., Tufail, Y., Finsterwald, M., Tauchmann, M. L., Olsen, E. J., Majestic, C., *Remote Excitation of Neuronal Circuits Using Low Intensity, Low Frequency Ultrasound*, PLoS One, 3(10):e3511; Bystritsky, A., Korb, A., Douglas, P., Cohen, M., Melega, W., Mulgaonkar, A., DeSalles, A., Min, B., Yoo, S. S., *A Review of Low Intensity Focused Ultrasound Pulsation*, Brain Stimulation, vol. 4, no. 3, pp. 125-136, (July 2011); Yoo, S. S., Bystritsky, A., Lee, J. H., Zhang, Y., Fischer, K., Min, B. K., McDannold., N. J., Pascual-Leone, A., Jolesz, F. A., *Focused Ultrasound Modulates Region-Specific Brain Activity*, NeuroImage, 56(3), 1267-75, (June 2011)). However, ultrasound is not known to produce significant effects on the peripheral nervous system sufficient to produce action events. See, e.g., Gavrilov L R, Geshuni G V, Il'iniskii O B, Popova L A, Sirotyuk M G, Tsirul'nikov E. M., *Stimulation Of Human Peripheral Neural Structures By Focused Ultrasound*, Sov Phys Acoust, 19(4):332-334 (1974); Colucci, V., Strichartz, G., Jolesz, F., Vykhodtseva, N., Hynynen, K., *Focused Ultrasound Effects on Nerve Action Potential*, Ultrasound in Medicine and Biology, Vol. 35. #10, pp. 1737-1747 (2009). Additionally it is well known that ultrasound passes through muscle tissue, even at elevated power levels, without producing direct stimulatory effects. There are, however, medical therapeutic applications that would be well served if ultrasound could be applied to the body in a method that would evoke physiologic changes.

The control of events during pregnancy and labor are generally understood to be under hormonal control, but there are certain bioelectrical effects associated with labor and delivery. For example, the underlying electrical activity of the uterine muscle produce the contractions associated with labor. However, bioelectric events are not thought to be associated with the progress of labor associated with changes in the cervix and cervical softening. Early changes in tensile strength during cervical softening result in part from changes in the number and type of collagen cross-links and are associated with a decline in expression of two matricellular proteins thrombospondin 2 and tenascin C.

Throughout early pregnancy, the cervix is rigid and thereby helps to maintain pregnancy by protecting the growing fetus within the uterine cavity. Normally, during the last one-half of pregnancy, the cervix slowly softens in preparation for birth at term. This process is generally termed cervical ripening. At term, the softened cervix is then capable of effacement and dilation to allow the baby to pass through the cervix and vagina during birth. Early cervical ripening often leads to premature birth (i.e., birth of the baby before the 37th week of gestation) and serious problems related to prematurity. On the other hand, delay in cervical ripening can result in still birth and seriously jeopardize the health of the baby or mother.

Presently, drugs such as prostaglandins and oxytocin are used to stimulate cervical ripening and labor near the end of gestation. It is estimated that about 40 to 60% of pregnant patients are treated with various prostaglandin agents to ripen the cervix and prepare patients for delivery. Thus, there is a large market for procedures which will ripen the cervix effectively. In the year 2000, the total sales for prostaglandins used to ripen the cervix was estimated to be $123 million in the USA. There are no present estimates but the total market today could approach well over $200 million dollars.

Remodeling of the cervix involves enzymatic dissolution of collagen fibrils, increase in water content, and chemical changes. These changes are known to be induced by hormones (estrogen, progesterone, relaxin), as well as cytokines, prostaglandins, and nitric oxide synthesis enzymes.

SUMMARY

According to an exemplary embodiment, a method of promoting cervical ripening comprises applying pulsed ultrasound energy to a cervix at a frequency, pulse duration, pulse repetition rate and peak pulse power sufficient to promote cervical ripening. In certain embodiments, the frequency range of the ultrasound energy is from 100 kHz to 10 MHz, the pulse duration is in the range of 1-50 milliseconds, the pulse repetition rate is in the range of 10-100 pulses per second, and the instantaneous peak pulse power ($I_{PPP}$) is in the range of 10-300 W/cm$^2$. The average power delivered is less than 720 m W/cm$^2$ and the ultrasound energy is applied from 10 minutes to 60 minutes.

According to another embodiment, the pulse duration is in the range of 10 microseconds to 300 microseconds and delivered in trains of 10-100 milliseconds bursts, the repetition rate is 1-25 Hz and the mechanical index (MI) is less than or equal to 1.9 and the $I_{SPTA.3}$ is less than 720 m W/cm$^2$.

In some embodiments, the ultrasound energy is applied to the face of the cervix via an intra-vaginal transducer. Alternatively, the ultrasound energy may be applied transabdominally to the cervix using a focused transducer, wherein the focal zone encompasses the cervix. The focal zone may encompass 60% of the cervix.

In accordance with other embodiments, other treatments, such as prostaglandin or other drugs to promote cervical ripening, may also be used, or ultrasound imaging using high frequency sound waves may be used to visualize the cervix before or following application of ultrasound energy that will soften (ripen) the cervix.

In other embodiments, a method of promoting cervical ripening comprises applying ultrasound energy to a cervix, wherein the parameters of the ultrasound energy are selected to promote cervical ripening. The parameters are selected from the group comprising: pulse frequency, pulse duration, pulse repetition frequency, and instantaneous peak pulse power. The pulsed ultrasound energy may be delivered by directing a focal zone of a focused ultrasound energy transducer towards a cervix or by directing a vaginal transducer towards a cervix.

In certain embodiments, a method of treating a cervix comprises applying pulsed ultrasound energy to a cervix, wherein a frequency of the pulsed ultrasound energy is 100 kHz to 10 MHz, a pulse duration of the pulsed ultrasound energy is 1-50 milliseconds; a pulse repetition rate of the pulsed ultrasound energy is 10-100 pulses per second; and a peak pulse power of the pulsed ultrasound energy is in the range of 10-300 W/cm$^2$. The frequency, pulse duration, pulse repetition rate, and peak pulse power may be selected to promote cervical ripening. The average power delivered may be less than 720 m W/cm$^2$, and the ultrasound energy may be applied from 10 minutes to 60 minutes.

In accordance with another embodiment, an apparatus for delivering ultrasound energy comprises an ultrasound transducer and a signal generator coupled to the ultrasound transducer to generate ultrasound energy. The signal generator is adapted to generate pulsed ultrasound energy with a frequency of 100 kHz to 10 MHz, a pulse duration of 1-50 milliseconds; a pulse repetition rate of 10-100 pulses per second; and a peak pulse power of 10-300 W/cm$^2$.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

In the following detailed description, reference is made to the accompanying drawings, in which are shown exemplary but non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims.

Figure 1:
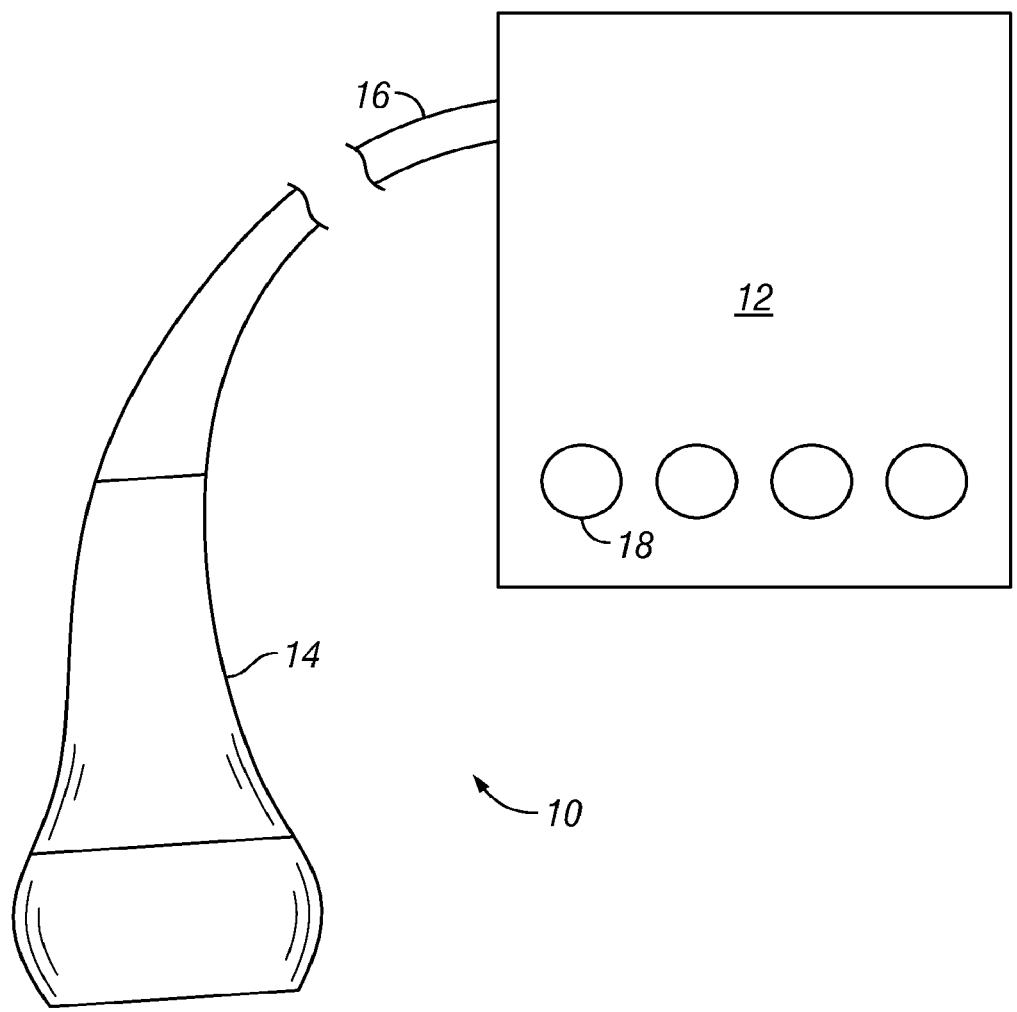
FIG. 1 is a schematic view of an apparatus for applying ultrasound energy to a cervix in accordance with an exemplary embodiment.

FIG. 1 shows a system 10 for applying pulsed ultrasound energy which may be used in accordance with an exemplary embodiment of the present invention. The system 10 includes a signal generator 12 which is coupled to a transducer 14 by a cable 16. The transducer 14 may be a focused transducer or an intra-vaginal transducer which uses, for example, a piezoelectric transducer to generate mechanical vibrations from electrical signals. The signal generator 10 generates a signal to drive the transducer to generate pulsed ultrasound and may include a power supply, a function generator, and an oscilloscope to generate and monitor a signal. The signal generator 10 has controls 18 to adjust the parameters (such as pulse frequency, pulse duration, pulse repetition frequency, and instantaneous peak pulse power) of the generated signal in accordance with the values described in further detail below. The system may be compact and implemented as a portable intra-vaginal applicator. The system may also be incorporated with or implemented by a ultrasound imaging system.

In accordance with an exemplary embodiment, ultrasound energy is applied to a cervix to promote cervical ripening. The ultrasound energy is applied with a specific pulse protocol that is selected to promote cervical ripening. The power level is comparable to that used in Ultrasound imaging. However, it differs from ultrasound imaging in that the ultrasound pulses are emitted at a lower repetition rate, have a longer duration than used in imaging, and are applied for overall a longer period of time than typical of imaging.

The application of ultrasound is directed so as to apply energy to the cervix while minimizing application of energy to surrounding tissue. One method of doing so is by using a focused ultrasound transducer that applies energy through the abdominal wall. The focused ultrasound transducer is positioned such that the focal zone encompasses the cervix. Preferably, at least 60% of the cervix is within the focal zone. However, the positioning of the beam is not critical, as evidenced by the testing described below. Another method of applying ultrasound energy is to use an intra-vaginal device to apply energy at the face of the cervix.

In one embodiment, ultrasound at 30-300 W/cm$^2$ is applied in the range of 1 to 50 millisecond pulses with a pulse repetition rate of 5 to 100 Hz such that the overall power level applied to tissue is less than 720 m W/cm$^2$ and therefore within generally accepted safe levels of ultrasound power. This power level is applied for a suitable duration, such as 10-60 minutes. Preferably, the power is applied for approximately 15 minutes.

In accordance with another embodiment, ultrasound pulses with a relatively shorter duration, 50 microseconds to 300 microseconds, are delivered in trains of 10-100 milliseconds bursts. The repetition rate is then 1-25 Hz, which is chosen to maintain an overall safe power delivery level. In this embodiment, the shorter duration pulses can use higher peak power values yet still remain within the range of safe MI and $I_{SPTA.3}$.

Additional therapies may be used in combination with ultrasound to promote the ripening of the cervix. For example, the ultrasound treatment may be combined with prostaglandin treatment or other drugs to promote cervical ripening.

The ultrasound ripening technique may also be performed in combination with traditional ultrasound imaging (i.e., applying high frequency sound waves).

EXAMPLE

A study was undertaken to characterize the effect of focused ultrasound (FUS) stimulation on a rat cervix as a means to produce ripening during pregnancy. Rat models are routinely used in studies of drugs used in humans for obstetrics and gynecology applications. Timed-pregnant Sprague-Dawley rats (Charles River Laboratories, Wilmington, Mass., USA) were housed separately. The rats were maintained on a constant 12 hours light and 12 hour dark cycle. The pregnant rats have a 22 day gestation cycle, day 1 being the day on which the sperm plug is observed. While undergoing focused ultrasound (FUS) treatment, the animals were anaesthetized with a combination of xylazine and ketamine based on their weight 1 µl/g. They were sacrificed by surgical dislocation for cervical tissue collection.

Figure 2:
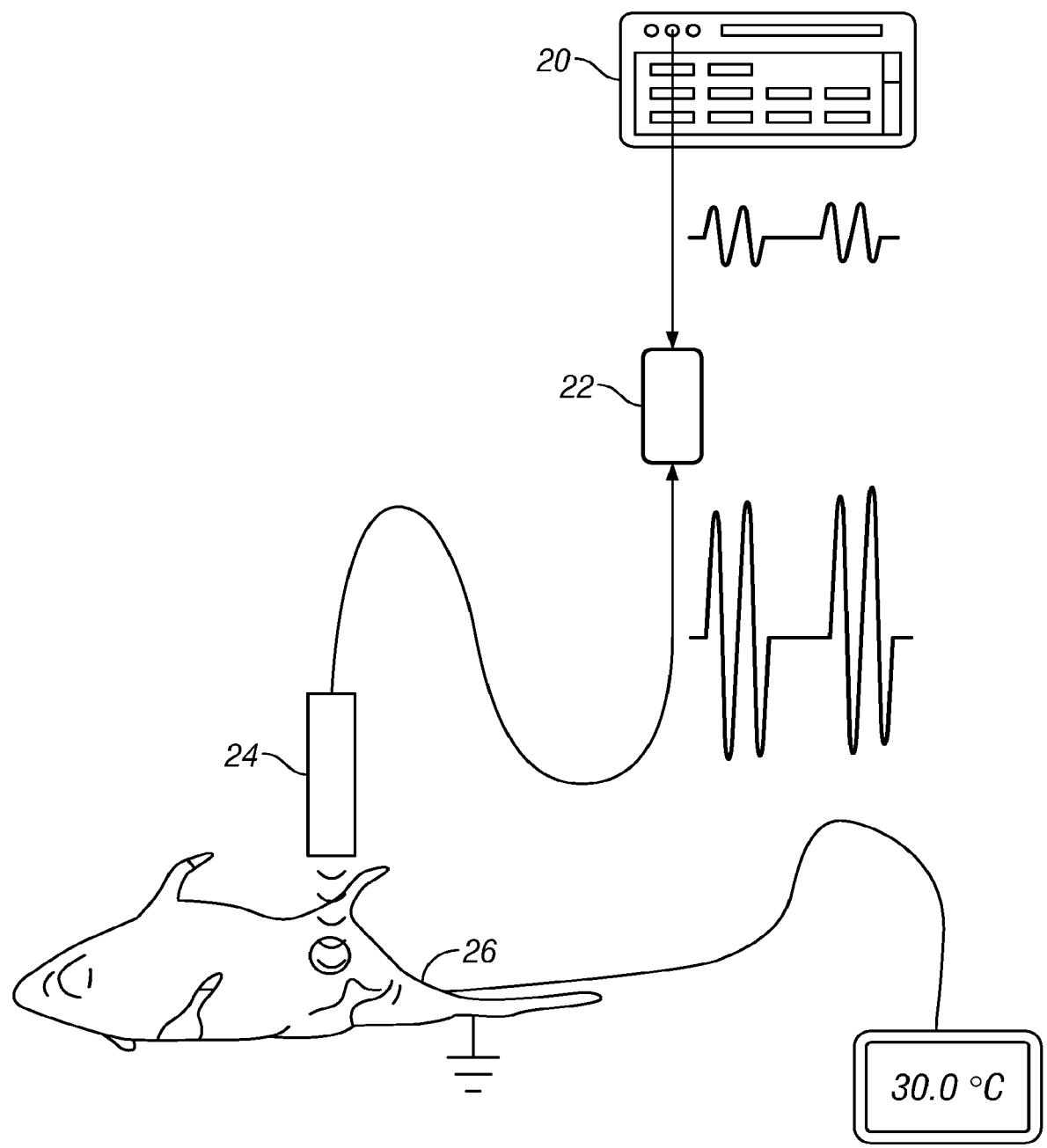
FIG. 2 is a schematic view of an apparatus used to construct and deliver pulsed ultrasound waveforms.
Figure 3:
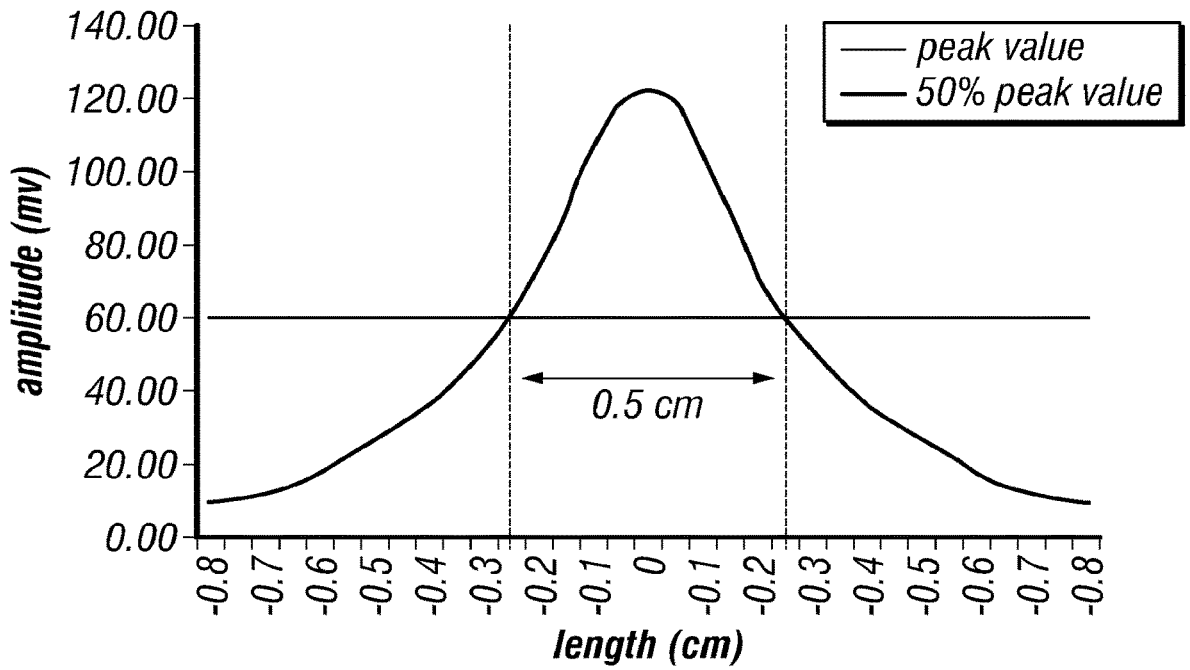
FIG. 3 is a graph showing focal zone power distribution.
Figure 4:
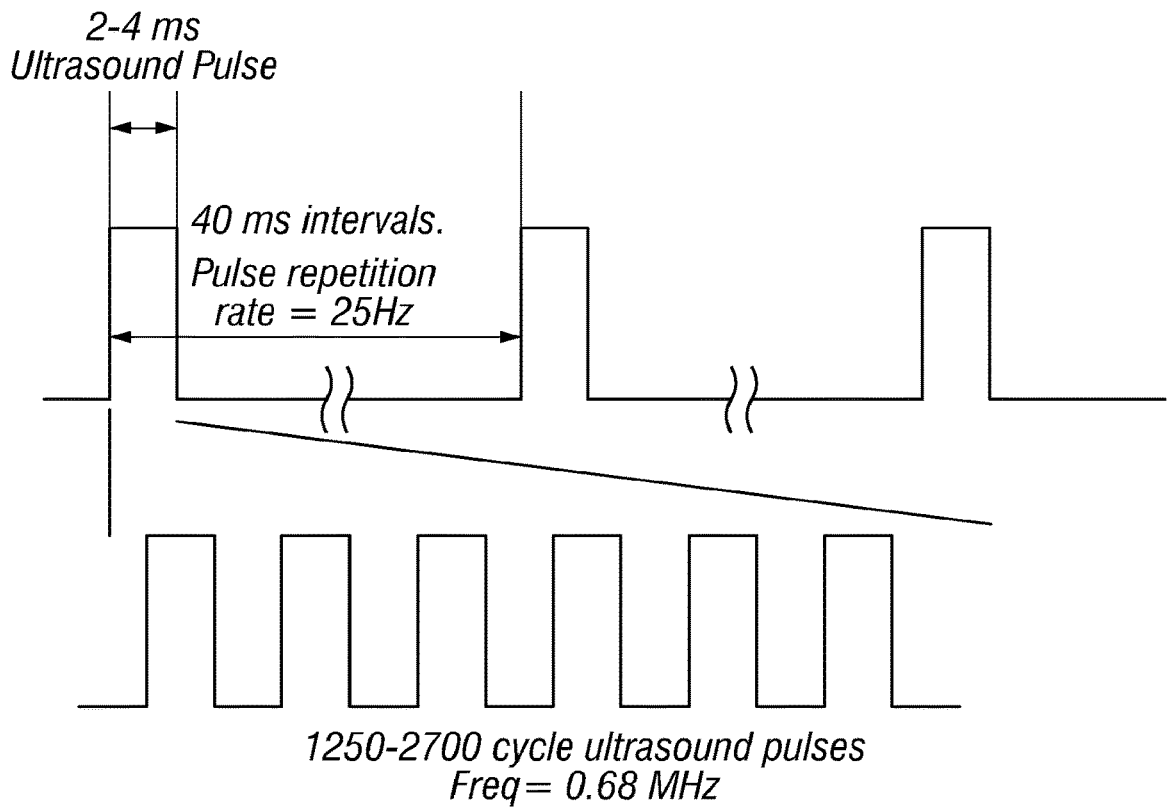
FIG. 4 is an exemplary low frequency ultrasound stimulus waveform.

A custom made ultrasound instrumentation set-up was constructed as illustrated in FIG. 2 to study the effects of FUS on cervix. A function generator 20 (Stanford. Research Systems DS-345) provided the excitation waveform as shown in FIG. 4. An ultrasound power amplifier 22 was built to drive a transducer 24 made from a 5 cm PZT disk (Steminc inc.) with a fundamental frequency of 0.682 MHz. The transducer was coupled to a spherically focused epoxy (West System Inc.) lens, having a 6.5 cm radius. The FWHM (full width at half maximum) of the output beam was approximately 5 mm diameter as measured by hydrophone (Precision Acoustics, Devonshire, UK). FIG. 3 shows the focal zone power distribution. A thermocouple 26 was used to measure temperature.

The ultrasound energy was applied through a water coupling column and acoustic coupling gel to the rat's abdominal skin surface over the cervix region as determined by palpation of an internal probe placed at the cervical entrance. The ultrasound beam passed through the annulus of the cervix in a parallel incidence to the plane of the cervix.

The experiment tested a range of ultrasound pulse widths at 680 KHz ultrasound using 25 Hertz pulse repetition rate as shown in FIG. 4.

As shown in Table 1, the $I_{SPPA}$ used in this experiment was measured at 40 W/cm$^2$ using continuous mode ultrasound and a force balance. The $I_{SPTA}$ varied from 1 W/cm$^2$ to 4 W/cm$^2$ by way of pulse durations from 1 millisecond to 4 milliseconds. The duration of ultrasound exposure time was in the range of 30 minutes to 1 hour.

TABLE 1

| Day of gestation when applied | Stimulation time (hour) | Frequency (KHz) | $I_{SPTA}$ (Watts/cm$^2$) | N = number of rats |
|---|---|---|---|---|
| D15 | 1 | — | 0 | 10 |
| D15 | 1 | 680 | 4 | 9 |
| D15 | 0.5 | 680 | 4 | 2 |
| D14 | 0.5 | — | 0 | 5 |
| D14 | 0.5 | 680 | 4 | 4 |
| D14 | 0.5 | 680 | 2 | 4 |
| D14 | 0.5 | 680 | 1 | 4 |
| Total | | | | 38 |

On day 14 or 15 of gestation, a focused ultrasound (FUS) system was placed on the abdominal surface of ketamine/xylazine anesthetized rats at the level of the internal cervix. In control rats, the FUS system was placed on the animals but no energy was applied. In treated rats, 680 kHz ultrasound at 25 Hertz repetition rate, 2-4 millisecond pulse duration was directed to the cervix from the skin for 0.5 to 1 hour. $I_{SPPA.3}$ was 40 W/cm$^2$, which is less than used in imaging (190 W/cm$^2$). The mechanical index (MI) of the ultrasound pulse was calculated to be 0.2 and so within safe regulatory limits (1.9).

A light-induced florescence (LIF) Collascope (Reproductive Research Technologies Inc., Houston, Tex.) was used to evaluate the changes in the elasticity of the cervix over time during gestation. LIF measurements were made on both experimental and control groups prior to ultrasound exposure. One hour after the beginning the FUS ultrasound treatment, the LIF test was performed again. LIF measurements were made on rats every 24 hours until their spontaneous delivery. The average of 16 measurements of fluorescent intensity at 390 nm wavelength was used to evaluate cervical ripening for each animal. Lower numerical values represent greater cervical ripening. After FUS, the cervix of animals was examined for mechanical changes and visually by endoscopic camera. Delivery times, fetal weights and fetal viability were made following delivery of both control and FUS-treated animals.

The effects of focused ultrasound on the cervix mechanical stretching and compliance were tested using a universal Tissue Organ Bath System (750TOBS, DMT, The cervix is defined as the least vascular tissue with two parallel lumina between the uterine horns and the vagina. Connective tissue and fat were removed and the cervix was suspended with its longitudinal axis vertically in a tissue bath chamber for tension recording. The chamber was filled with physiological Kreb's solution, bubbled with a mixture of 95% O2 and 5% CO2, and maintained at 37° C. The isolated cervix was elongated incrementally at 0.10 the rate of 0.0.15 mm/s and tension continuously recorded. The slope of the regression line through the linear portion of the length-tension curve was employed as an indication of the cervical extensibility. The slope of the length-tension curve is linearly related to cervical resistance.

Statistical comparisons between two group data were estimated by unpaired student's t-test analysis. A 2-tailed probability value of P<0.05 was considered to be statistically significant different. Results are expressed as means±SEM.

A total of 38 rats were used in the study according to Table 1 where the day of gestation is listed on the left.

Figure 5:
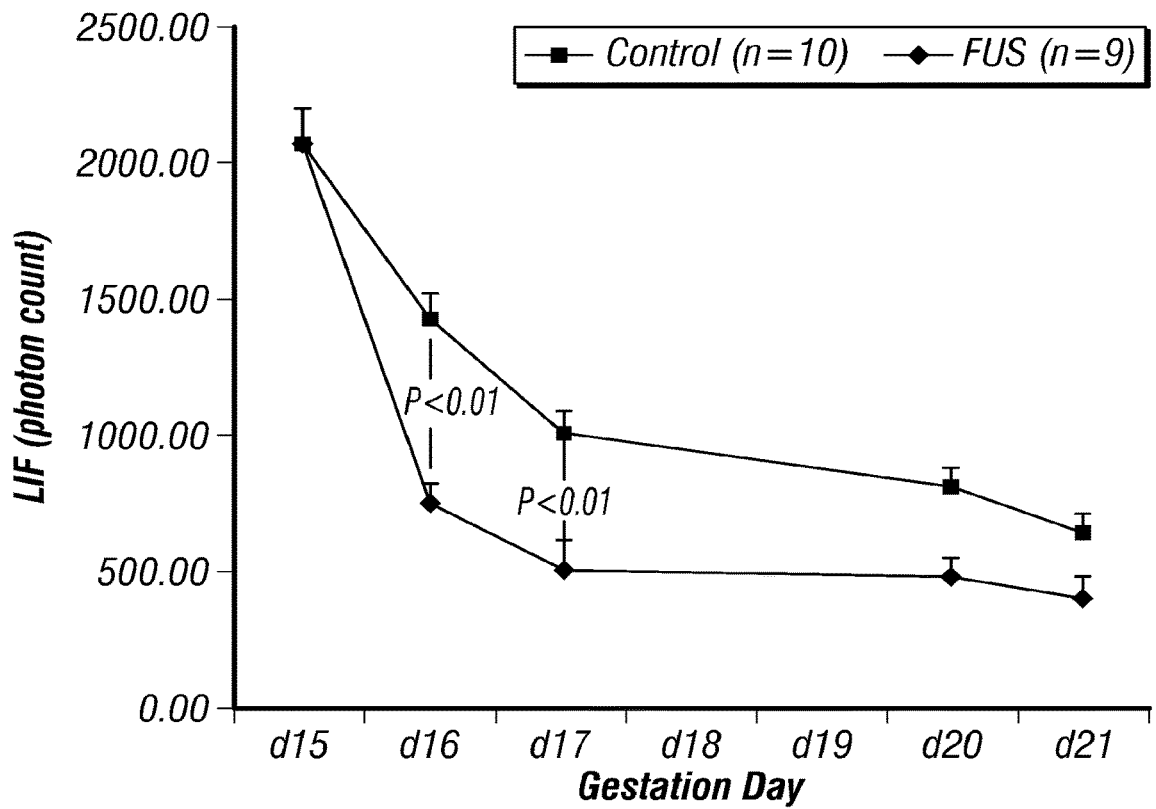
FIG. 5 is a graph of daily light-induced florescence (LIF) measurement during gestation in treated rats versus control rats.

FIG. 5 plots the cervical ripening as determined by the LIF for ultrasound treated (n=9) animals and for untreated control (n=0.10) animals and for treatment duration of 1 hour at 4 milliseconds ultrasound pulse width. This plot starts at gestation day 15 when FUS stimulation was applied until spontaneously delivery on day 22.

The time of delivery of controls and treated groups were determined as hours after 8 AM of day 22 of gestation. The expulsion of 1 pup was defined as delivery. In control animals as seen in FIG. 5 the cervical LIF values drop with the normal progressive ripening from day 15 of gestation to day 21.

In the ultrasound treated group LIF values dropped faster from the control value of 2064±116 on day 15 and continued to decline after treatment to delivery at 637±133 which is lower than control.

The ultrasound treatment produced LIF values significantly lower (P<0.01) in FUS treated animals on days 16 and 0.17 that are immediately after ultrasound treatment when compared to controls (day 16: 700±237 versus control 1319±241 day 17: 503±231 versus control 1000±178). The LIF values for the treated group remain low until delivery.

Figure 6:
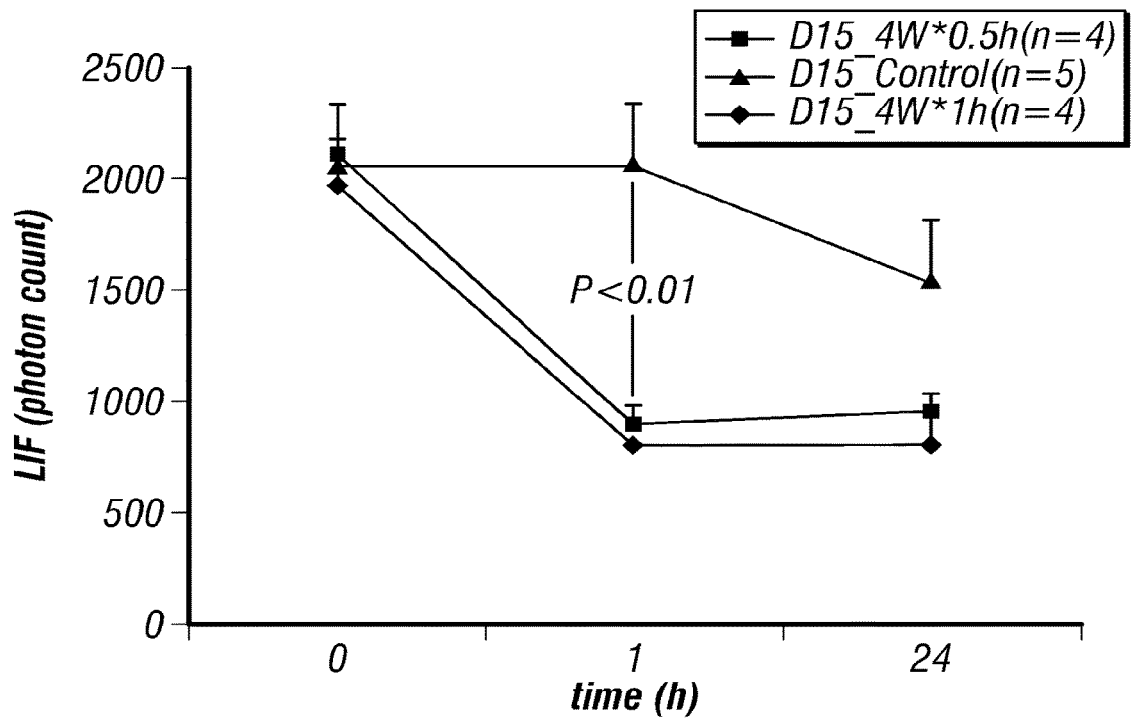
FIG. 6 is a graph showing changes in LIF after focused ultrasound application as a function of exposure time.

A series of experiments were performed on day 15 for both 30 minute and 1 hour at 4 W/cm$^2$. After 24 hours and LIF tests, the rat cervix was collected and mechanical tests of cervical resistance were performed. FIG. 6 shows this result. Ultrasound had a strong cervical ripening effect measured at 1 hour after the beginning of stimulation compared to control (1 hour: 806±90, 0.5 hour: 897±99, compared to control: 2059±122) and this was 0.10 sustained over the 24 hour observation interval. The amount of ripening produced by ultrasound at this stage of pregnancy was greater than that of control. Additionally, longer 1 hour exposures compared to 30 minutes did not appear to produce an additional ripening effect. Further testing has shown that ripening is initiated with durations of 20 minutes, and some trial data suggests 10 minutes may be sufficient.

Figure 7:
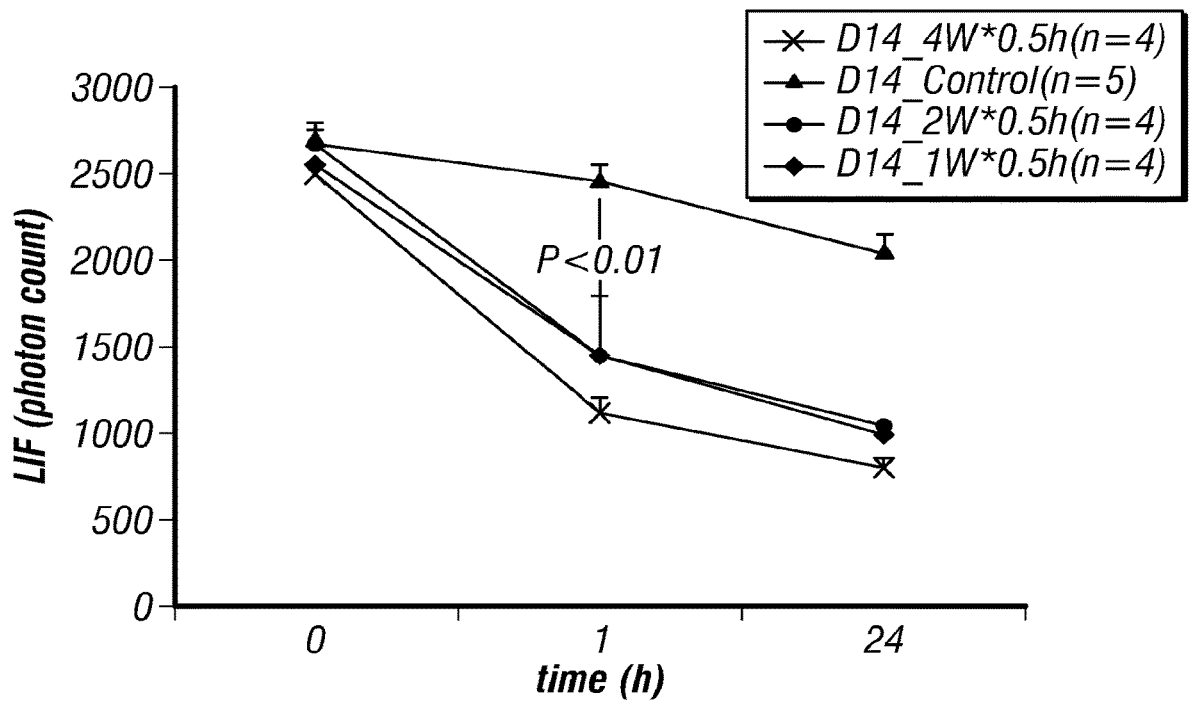
FIG. 7 is a graph showing changes in LIF after focused ultrasound application as a function of power level.

An additional series of experiments were directed to measuring the effects of power level. This series consisted of 30 minute ultrasound exposure commencing on day 14 using three different power levels (0.1 W/cm$^2$, 2 W/cm$^2$, 4 W/cm$^2$). FIG. 7 shows a large and significant cervical change (P<0.01) at power levels of 1 W/cm$^2$: 1454±349, 2 W/cm$^2$: 1458±103, 4 W/cm$^2$: 1119±89 compared to control of 2467±126 at one hour after exposure.

Figure 8:
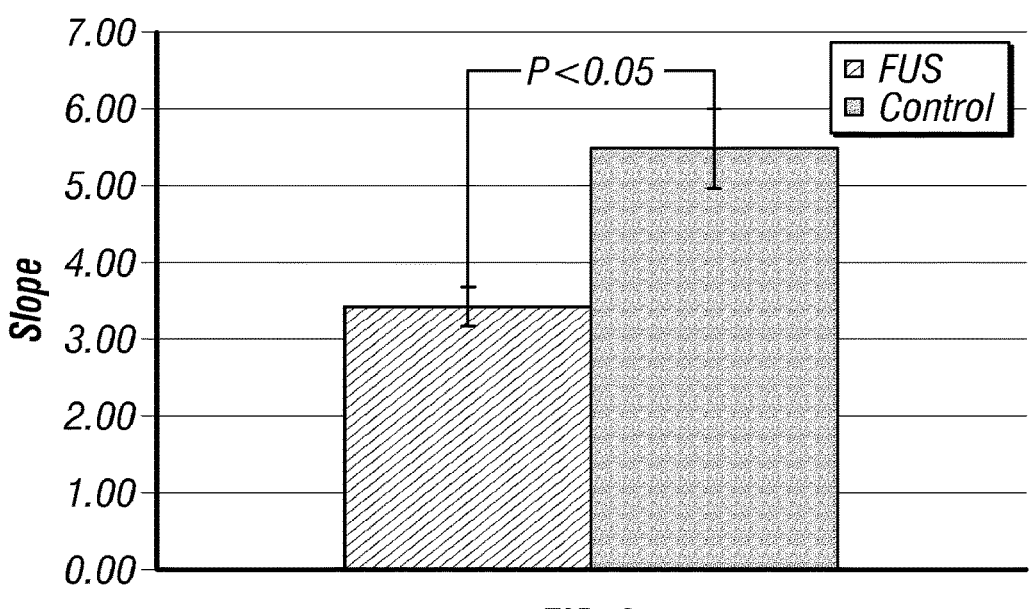
FIG. 8 is a graph showing stretch test results showing the effect of ultrasound on a cervix.

FIG. 8 shows the stretch test result for cervical ripening for treated and control groups. Confirming the result above, there is significantly increased cervical extensibility of the ultrasound treated group compared to the control group.

Figure 9:
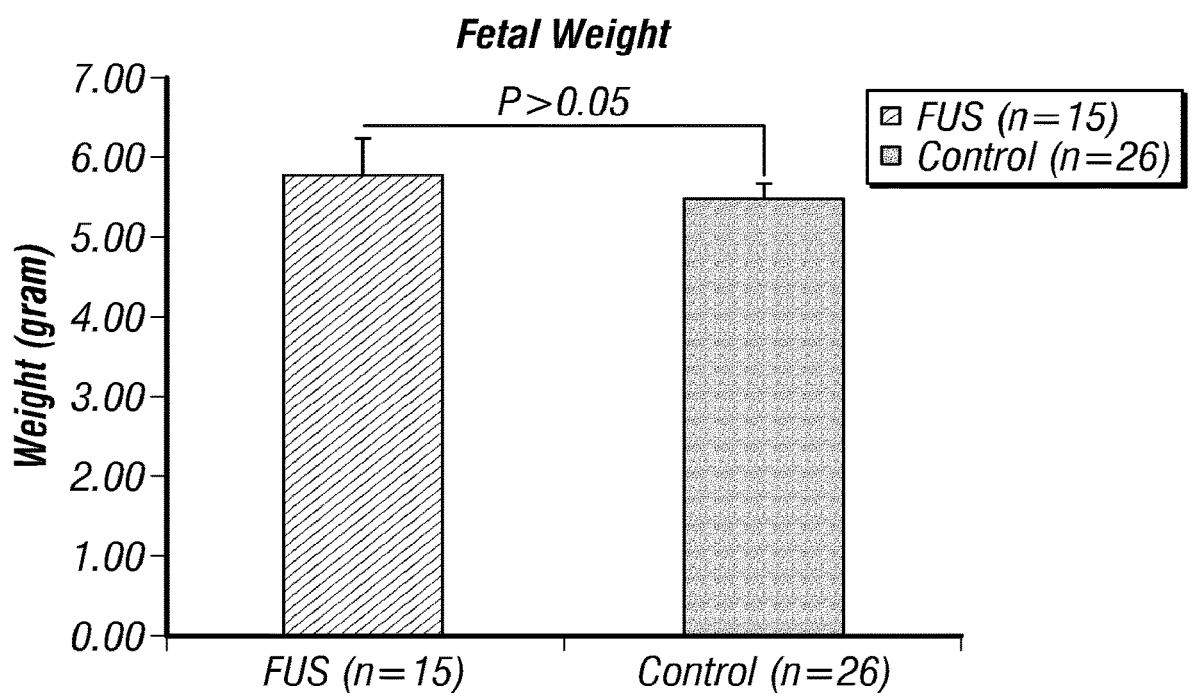
FIG. 9 is a comparison of fetal delivery weights of ultrasound treated and control groups.

FIG. 9 shows that the FUS treated groups have no change in the average weight (grams) of fetus of control and treated groups (FUS: 5.81±0.43 VS Control: 5.41±0.25). We observed no preterm births in the treated group. All fetuses were delivered within 24 hours after 8 am of day 22.

These studies show that focused ultrasound of the listed pulse characteristics produced a significant effect on the rat cervix to produce early softening or ripening. The physical basis of this effect is unclear and unexpected in view of the scientific literature of ultrasound bioeffects.

The softening of the cervix normally is a gradual and progressive process occurring during the last half of gestation cycle. This finds that the process of cervical ripening can be substantially accelerated by application of ultrasound and comparable to a level to animals during normal spontaneous that of delivery at term.

In this study 680 kHz ultrasound effects occur after as little as 30 minutes exposure and at power levels as low as 1 W/cm². The lower threshold of this ultrasound cervical bioeffect was not determined in this study, and lower values may be satisfactorily used. The effects at 4 W/cm² were statistically the same as 1 W/cm² and power levels below this were not tested.

By comparison, ultrasound imaging systems typically use 3-6 MHz frequencies and microsecond-order pulse widths at kilohertz repetition rate. The difference in pulse characteristics is likely the reason for the physiologic effects of FUS on cervical ripening since ultrasound imaging systems are not known to produce physiologic changes.

The largest of the ultrasound induced physiologic change is seen within tens of minutes after stimulation. This is in contrast to the much slower process of ripening occurring over the last seven to eight days during normal pregnancy. The ultrasound induced cervical ripening was verified by a mechanical stretch test of extensibility.

Experiments show that ultrasound decreased the time course of cervical ripening which was then sustained over the 8 days prior to delivery and did not reverse back to a rigid state. The induced cervical ripening appears to be irreversible. We note that the early cervical ripening did not produce preterm birth or delay birth even though the treated group had a cervix soft enough to allow delivery.

The relatively rapid ripening of the cervix by ultrasound is much faster than the typical application of prostaglandins that need 12 hours to promote cervical ripening in the clinic with women as is conventional treatment. This could be a substantial advantage of the ultrasound technique in that it could be applied clinically to achieve ripening before delivery. The ultrasound energy in these experiments was focused to the cervix and this would suggest little or no effects on other body systems.

Acoustic Intensity Calculation

The pulse characteristics of ultrasound in this study were long compared to imaging systems but slow in repetition rate. The total ultrasound dose was comparable to imaging systems and to safe regulatory guidelines. Ultrasound power level is a function of both its intensity and time of application. Spatial-peak pulse-average intensity ($I_{SPPA}$) is defined as:

$$I_{SPPA} = \frac{PII}{PD}$$

Where PD is the pulse duration defined as (t).

The $I_{SPPA}$ was tested through force balance to be 40 W/cm². Spatial-peak temporal-average intensity ($I_{SPTA}$) is defined as:

$$I_{SPTA} = PII(PRF)$$

Where PRF is pulse repetition frequency, which is represented in Hertz.

The pulse intensity integral (PII) is defined as:

$$PII = \int \frac{p^2(t)}{z_0} dt$$

Where $p_c$ is the instantaneous peak pressure, $Z_0$ is the characteristic acoustic impedance in Pa·s m-1 defined as ρc, where ρ is the density of the medium and c is the speed of sound in the medium. ρ was estimated to be 0.1028 kg m-3 and c to be 1515 in s-1 for tissue on the basis of previous reports. $p_r$ was calculated to be 158 KPa.

The mechanical index (MI) was calculated by:

$$MI = \frac{p_r}{\sqrt{f}}$$

where $p_r$ is the peak rare-factional pressure and f is the acoustic frequency.

From these relationships the $I_{SPPA}$ is calculated at 40 W/cm² while the FDA regulatory limit is 190 W/cm² for both the body periphery as well as the fetus. The mechanical index is calculated at 0.2 and so within the FDA limitation of 1.9. FDA regulations define ultrasound power levels in terms of power at the target organ $I_{SPPA.3}$ where the .3 indicates the derated power. Currently the FDA $I_{SPTA.3}$ regulatory limit on diagnostic imaging systems to organs in the body periphery is presently 720 m W/cm² (ODRH, 2008). The $I_{SPTA.3}$ was unknown in this study but would be less than 1 W/cm² because of transducer coupling losses and attenuation of ultrasound as its passes through the tissues of the rat body.

As recognized by one skilled in the art, there are many variables that might be optimized in an effort to achieve lower yet effective ultrasound power. The lowest effective power is likely to be below that tested in this study since even 1 W/cm² was as effective as the highest tested power at 4 W/cm².

The mechanism of action for ripening of the cervix by the application of ultrasound energy is not generally understood at this time. Without being bound by any particular theory, it has been postulated that FUS may include activation of neural and biochemical pathways or direct fragmenting collagen Vii-bridges.

One theory is that ultrasound does not directly affect the collagenous structure of the cervix but rather triggers a bioelectrical activation that then causes a cascade of events that affect it indirectly. Another theory is that ultrasound may trigger the release of cytokines that then result in the ripening process.

Another theory depends on the known stretch sensitivity of the cervix. Mechanical stretching actuates natural physiologic responses and this may initiate cervical maturation. For example, Takemura et al. (M. Takemural, H. Itoh, N. Sagawa, S. Yura, D. Korita, K. Kakuil, M. Kawamural, N. Hirota, H. Maeda and S. Fujii, "Cyclic mechanical stretch augments hyaluronan production in cultured human uterine cervical fibroblast cells", Molecular Human Reproduction Vol. 11, No. 9 pp. 659-665, 2005) report that mechanical stretching of cervical cells in culture causes a biochemical cascade of events that ultimately releases hyaluron, a biochemical associated with cervical collagen.

Pulses of ultrasound in the repetition range of 5-200 Hz as practiced by this invention, create a periodic radiation pressure at the pulse repetition rate. Soft tissue at the beam focus is stretched at this pulse rate compared to the ultrasound carrier wave. In the above described study, for example, the data was generated using a modulation frequency of 25 Hz. Thus pulsed ultrasound may initiate a cascade of biochemical events by way of the stretch sensitivity of cervical tissue and thus promote cervical maturation.

A further theory is that most physiological processes within the body have bioelectrical correlates and processes can be modulated in their function by application of small electrical currents. Ultrasound energy is known to affect bioelectrical events in the CNS and have some effects on the PNS. Thus the observed effects of ultrasound on the cervix may be through interaction with a local nerve plexus that then promotes the local or more distant release of endogenous prostaglandin.

Furthermore, although bioelectrical events are not known to be associated with cervical ripening, that there is the possibility and that the effects of ultrasound could be through a known bioelectrical interaction with nerves (see, e.g., Gavrilov L R, Geshuni G V, Il'iniskii O B, Popova L A, Sirotyuk M G, Tsirul'nikov E. M., *Stimulation Of Human Peripheral Neural Structures By Focused Ultrasound*, Soy Phys Acoust, 19(4):332-334 (1974); Mihran, R., Barnes, F., Wachtel, H., *Temporally Specific Modification of Myelinated Axon Excitability In-Vitro Following a Single Ultrasound Pulse*, Ultrasound in Med. Biol. vol. 16, No. 3., pp. 297-309 (1990); Colucci, V., Strichartz, G., Jolesz, F., Vykhodtseva, N., Hynynen, K., *Focused Ultrasound Effects on Nerve Action Potential*, Ultrasound in Medicine and Biology, Vol. 35. #10, pp. 1737-1747 (2009)) and these may trigger cervical hormonal release.

The invention claimed is:

1. A method for producing cervical ripening in a pregnant patient, the method comprising:
   generating a pulsed ultrasound signal having parameters in a combination configured to promote cervical ripening, the parameters including a frequency ranging from 100 kHz to 10 MHz, a pulse duration ranging from 1 to 50 milliseconds, a pulse repetition rate ranging from 1 to 25 pulses per second, and an instantaneous peak pulse power ranging from 10-300 W/cm$^2$;
   applying the pulsed ultrasound signal to the patient's cervix for a duration between 10 minutes and 60 minutes; and
   producing ripening of the patient's cervix in response to the applied pulsed ultrasound signal.

2. The method of claim 1, wherein applying the pulsed ultrasound signal includes applying the pulsed ultrasound signal through the patient's abdominal wall with an ultrasound transducer.

3. The method of claim 2, wherein the ultrasound transducer is a focused ultrasound transducer, and further comprising directing a focal zone of the focused ultrasound transducer toward the patient's cervix.

4. The method of claim 3 further comprising directing the focused ultrasound transducer so that at least 60% of the patient's cervix is within the focal zone.

5. The method of claim 1 further comprising directing an intra-vaginal transducer toward the patient's cervix.

6. The method of claim 5, wherein the applying the pulsed ultrasound signal includes applying the pulsed ultrasound signal to a face of the patient's cervix via the intra-vaginal transducer.

7. The method of claim 1, wherein the pulse duration is delivered in trains of 10-milliseconds to 100-milliseconds bursts.

8. The method of claim 1, further comprising generating the pulsed ultrasound signal having an average power less than 720 mW/cm$^2$.

9. The method of claim 1, further comprising treating the patient with prostaglandins to further promote cervical ripening.

10. The method of claim 1, wherein the duration is between 10 minutes and 30 minutes.

11. The method of claim 1 further comprising visualizing the cervix one of before and after producing ripening using ultrasound imaging.

* * * * *

UNITED STATES PATENT AND TRADEMARK OFFICE
CERTIFICATE OF CORRECTION

PATENT NO. : 11,058,900 B2
APPLICATION NO. : 15/820838
DATED : July 13, 2021
INVENTOR(S) : Bruce C. Towe et al.

Page 1 of 1

It is certified that error appears in the above-identified patent and that said Letters Patent is hereby corrected as shown below:

In the Specification

Column 8, Line 27, "0.17 that" should be --17 that--.

Column 8, Line 38, "was 0.10 sustained" should be --was sustained--.

Column 10, Line 40, "Vii-bridges" should be --X-bridges--.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*